United States Patent
Barr et al.

(10) Patent No.: US 8,561,226 B1
(45) Date of Patent: Oct. 22, 2013

(54) MRI OR IMAGING TRANSFER TABLE

(75) Inventors: Rodney Barr, Cary, NC (US); Michael Bruce Wiggin, High Point, NC (US)

(73) Assignee: Martin Manufacturing Co., Inc., Rocky Mount, NC (US)

( * ) Notice: Subject to any disclaimer, the term of this patent is extended or adjusted under 35 U.S.C. 154(b) by 476 days.

(21) Appl. No.: 12/828,547

(22) Filed: Jul. 1, 2010

Related U.S. Application Data (60) Provisional application No. 61/222,319, filed on Jul. 1, 2009.

(51) Int. Cl.
*A61G 5/00* (2006.01)
*A47C 27/08* (2006.01)
*A47C 21/08* (2006.01)
*A47B 13/00* (2006.01)

(52) U.S. Cl.
USPC .................. 5/81.1 R; 5/601; 5/424; 5/425

(58) Field of Classification Search
USPC ............... 5/81.1 R, 600, 601, 658, 424–430
See application file for complete search history.

(56) References Cited

U.S. PATENT DOCUMENTS

| | | | | | |
|---|---|---|---|---|---|
| 3,293,668 | A | * | 12/1966 | Auer | 5/81.1 HS |
| 3,304,116 | A | * | 2/1967 | Stryker | 296/20 |
| 3,810,264 | A | * | 5/1974 | Mueller | 5/220 |
| 4,105,923 | A | * | 8/1978 | Hynes, Jr. | 378/20 |
| 4,222,132 | A | * | 9/1980 | Crim et al. | 5/81.1 R |
| 4,568,071 | A | * | 2/1986 | Rice | 5/601 |
| 4,987,623 | A | * | 1/1991 | Stryker et al. | 5/86.1 |
| 5,131,103 | A | * | 7/1992 | Thomas et al. | 5/601 |
| 5,197,156 | A | * | 3/1993 | Stryker et al. | 5/428 |
| 5,477,570 | A | * | 12/1995 | Hannant et al. | 5/86.1 |
| 6,026,318 | A | * | 2/2000 | Bernstein et al. | 600/427 |
| 6,101,644 | A | * | 8/2000 | Gagneur et al. | 5/81.1 R |
| 6,675,415 | B2 | * | 1/2004 | Wong | 5/601 |
| 6,768,916 | B2 | * | 7/2004 | Heinold et al. | 600/415 |
| 6,782,571 | B1 | * | 8/2004 | Josephson et al. | 5/601 |
| 6,862,759 | B2 | * | 3/2005 | Hand et al. | 5/430 |
| 6,978,499 | B2 | * | 12/2005 | Gallant et al. | 5/600 |
| 7,131,769 | B2 | * | 11/2006 | Vezina | 378/209 |
| 7,181,791 | B2 | * | 2/2007 | Clayton | 5/600 |
| 7,216,383 | B2 | * | 5/2007 | Heinl et al. | 5/601 |
| 7,568,241 | B2 | * | 8/2009 | Roberts | 5/81.1 R |
| 7,571,498 | B2 | * | 8/2009 | Jewell et al. | 5/81.1 HS |
| 7,676,861 | B2 | * | 3/2010 | Ward et al. | 5/428 |
| 7,874,030 | B2 | * | 1/2011 | Cho et al. | 5/601 |
| 8,176,584 | B2 | * | 5/2012 | Hornbach et al. | 5/601 |
| 2005/0060804 | A1 | * | 3/2005 | Heinl et al. | 5/601 |
| 2007/0000056 | A1 | * | 1/2007 | Ward et al. | 5/611 |
| 2007/0124858 | A1 | * | 6/2007 | Ahlman | 5/81.1 R |
| 2007/0220672 | A1 | * | 9/2007 | Roberts | 5/81.1 R |
| 2008/0276370 | A1 | * | 11/2008 | Van Es et al. | 5/81.1 R |
| 2010/0071127 | A1 | * | 3/2010 | Koger et al. | 5/81.1 HS |

* cited by examiner

*Primary Examiner* — William Kelleher
*Assistant Examiner* — Eric Kurilla
(74) *Attorney, Agent, or Firm* — Coats and Bennett, PLLC (57) ABSTRACT

An MRI transfer table is provided for transporting a patient and transferring a patient to an MRI table associated with an MRI apparatus. The MRI transfer table includes a mobile frame, a patient support and a series of connectors for detachably connecting the patient support to the mobile frame. In use, the MRI transfer table is aligned with the MRI apparatus and the MRI table is projected underneath the patient support of the MRI transfer table. The patient support is disconnected from the mobile frame and allowed to rest on the MRI table. Thereafter the mobile frame is moved from the MRI apparatus and the MRI table with the patient support thereon retracted into the MRI apparatus.

17 Claims, 11 Drawing Sheets

MRI OR IMAGING TRANSFER TABLE

CROSS-REFERENCE TO RELATED APPLICATION

This application claims priority under 35 U.S.C. §119(e) from the following U.S. provisional Application Ser. No. 61/222,319 filed on Jul. 1, 2009. That application is incorporated in its entirety by reference herein.

FIELD OF THE INVENTION

The present invention relates to safety transfer devices for transferring patients from one structure to another, and more particularly to a transfer table for transferring a patient onto the table of an MRI apparatus.

BACKGROUND OF THE INVENTION

The many problems dealing with the safe transfer of patients from one structure to another are well documented. Not only is there a danger in harming the patient but recent studies have shown a substantial increase in injuries incurred by nurses, attendants and other healthcare providers in connection with transferring patients from, for example, beds, tables and wheelchairs to another support device. This is especially true in handling obese patients.

This problem exists in many areas but one area that has not received a great deal of attention is the problem of transferring non-mobile patients from a stretcher to an MRI table. There are transfer boards used to transfer patients from a stretcher to an MRI table. But still, nurses and other attendants and healthcare professionals have to pull or lift the patient from the stretcher onto the MRI table. In some cases transfer devices have been employed that comprise sheet material of a relatively low friction that is used to slide the patient from the stretcher to the MRI table. But again the patient has to be pulled and physically moved from the stretcher to the MRI table. There are other patient transfer devices but they are not compatible with MRI tables. For a more comprehensive review of the prior art in patient transfer and handling systems, see Exhibit 1 attached, the contents of which are expressly incorporated herein by reference.

SUMMARY OF THE INVENTION

The present invention entails an MRI transfer table comprising a mobile frame, a patient support, and a series of connectors for detachably connecting the patient support to the mobile frame. In use, the MRI transfer table is aligned with the MRI table such that the patient support is elevated slightly higher than the top surface of the MRI table. The MRI transfer table includes a generally open front frame structure that enables the MRI table to be projected underneath the patient support. The MRI table is raised such that the top surface lies just below the bottom surface of the patient support. Through a series of connectors, the patient support is disconnected from the mobile frame, leaving the patient support supported on the top surface of the MRI table. Now the mobile frame, without the patient support, can be retracted, leaving the patient supported on the MRI table.

BRIEF DESCRIPTION OF THE DRAWINGS

FIGS. 3-8 are a sequence of views showing how the MRI transfer table is used in conjunction with an MRI apparatus.

DESCRIPTION OF EXEMPLARY EMBODIMENTS

Figure 1:
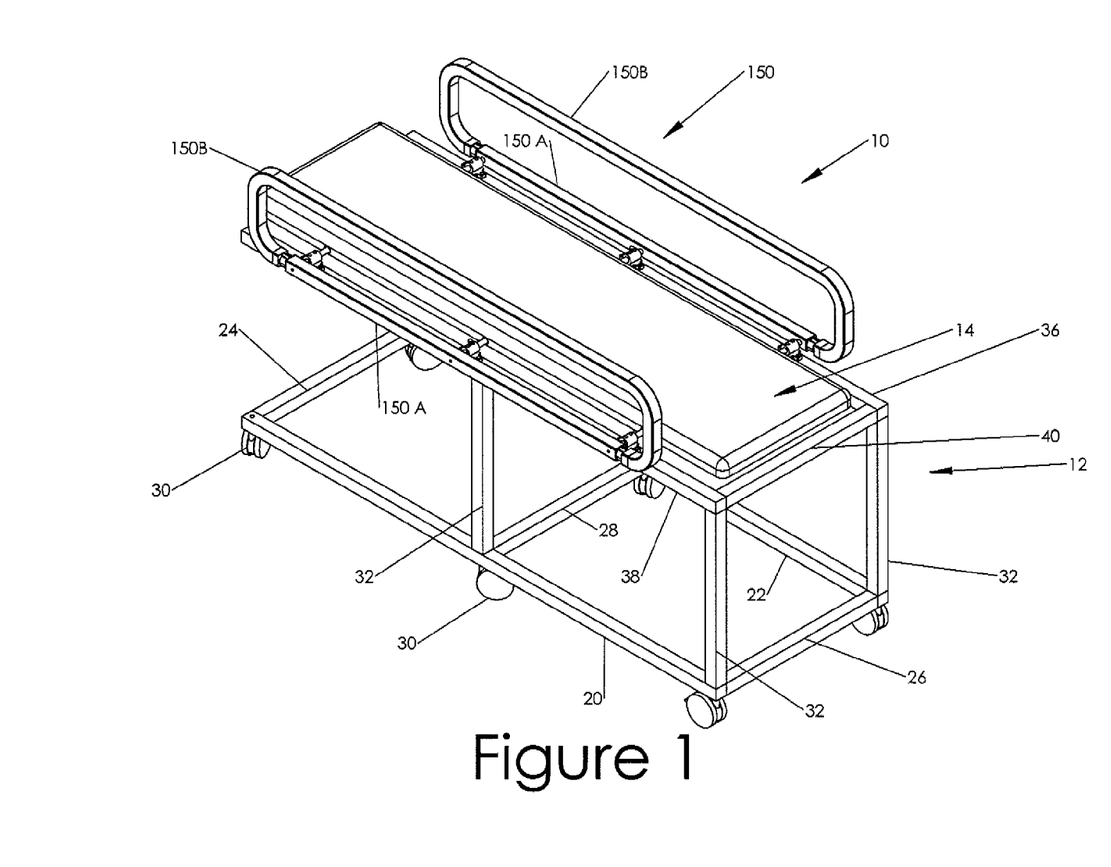
FIG. 1 is a perspective view of the MRI transfer table.
Figure 2:
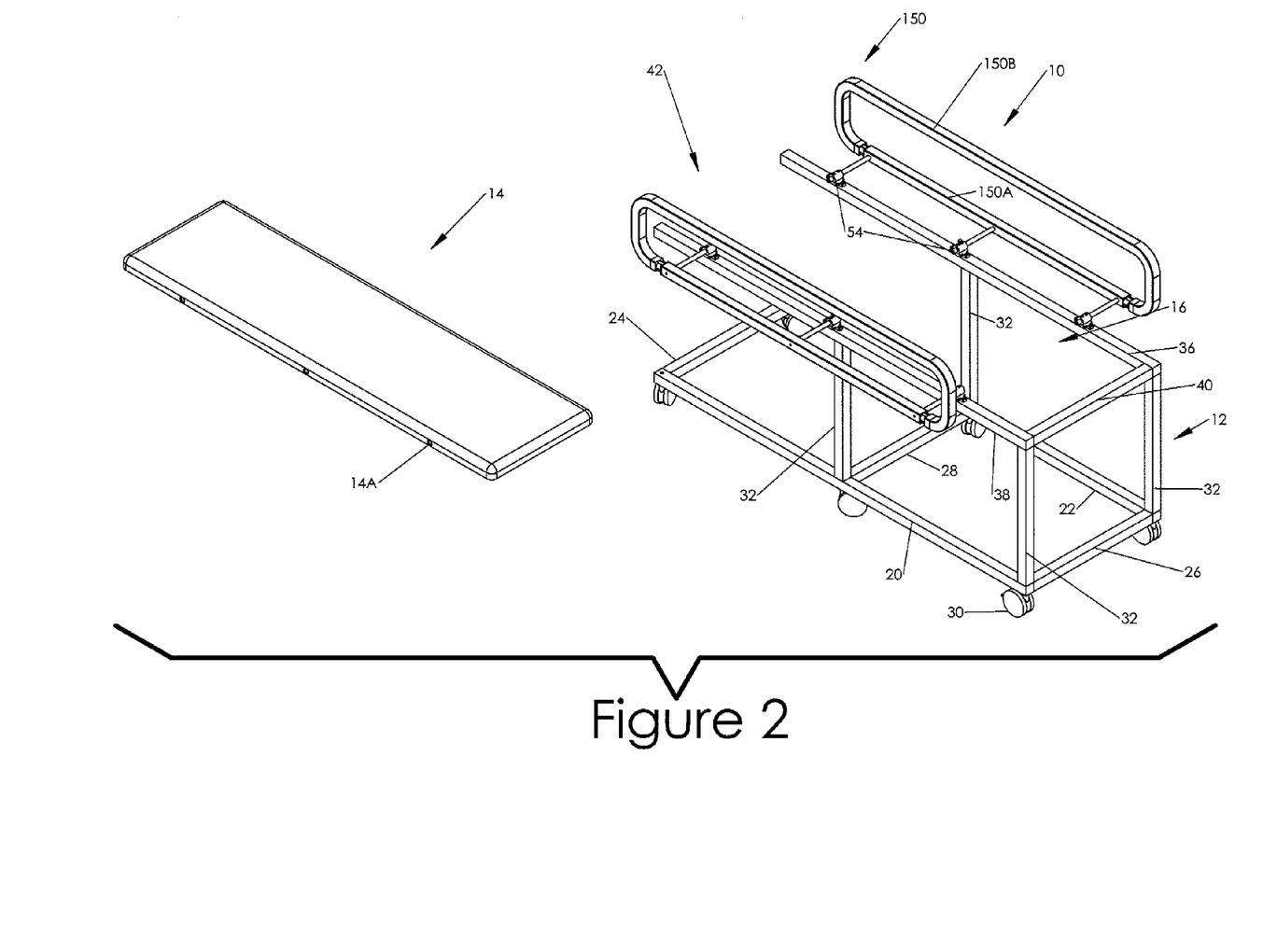
FIG. 2 is a perspective view of the MRI transfer table with the patient support removed from the mobile frame structure.

With further reference to the drawings, particularly FIGS. 1 and 2, the MRI transfer table is shown therein and indicated generally by the numeral 10. As used herein, the term "MRI" means a medical imaging device, system or apparatus. Therefore, the MRI transfer table includes a transfer table designed to transfer a patient to a CT scanning device for example, or to any medical imaging device. MRI transfer table 10 includes a mobile frame structure indicated generally by the number 12, a patient support indicated generally by the numeral 14, and a series of connectors, each indicated generally by the numeral 16 where the connectors function to detachably connect the patient support 14 to the mobile frame 12.

Turning to the mobile frame structure 12, the frame structure includes a lower base frame, which in one embodiment illustrated, includes side members 20 and 22, and end members 24 and 26. An intermediate member 28 extends transversely across and between the side members 20 and 22. Various types of materials can be utilized for the mobile frame structure 12, but in the embodiment illustrated herein, the structural members comprising the frame structure are metal. Further, the particular elements or members constituting the mobile frame structure 12 can be secured together by conventional means including weldment, bolts and other types of fasteners. Secured to the lower base frame is a series of wheels 30. In the embodiment illustrated herein there is provided a wheel on each corner of the lower frame and a wheel adjacent opposite ends of the intermediate member 28.

Extending upwardly from the lower base frame is a series of upright posts 32. Note that there are two upright posts 32 extending upwardly from one end portion of the lower base frame and another pair of upright posts 32 extending upwardly intermediately the base frame adjacent the intermediate member 28.

Also forming a part of the mobile frame structure 12 is an upper frame. The upper frame is supported by the uprights 32. Note in FIG. 1 where the left most end of the upper frame is open about one end. More particularly, the upper frame includes a pair of parallel side members 36 and 38. About one end of the upper frame there is provided an end member 40 that extends across and between side members 36 and 38. See FIG. 2. Opposite end member 40 is an open end indicated by the numeral 42. See FIG. 2.

Supported on the mobile frame structure 12 is a patient support indicated generally by the numeral 14. In the embodiment illustrated herein the patient support 14 is elongated and is constructed of non-metallic material. In various embodiments the patient support 14 is constructed of wood or plastic, or a combination of wood and plastic, and may include an outer upholstered surface.

The MRI transfer table 10 includes a plurality of connectors 16 for detachably connecting the patient support 14 to the mobile frame structure 12. As will be appreciated from subsequent portion of this disclosure, the connectors 16 include a series of pins that are supported on the mobile frame structure 12 and which project into apertures or receivers in the side edges of the patient support 14. In an attached position, the pins project into the apertures or receivers of the patient support 14. In a detached position, the pins are retracted from the apertures and the patient support 14 can be moved independently of the mobile frame structure 12.

Continuing to refer to the drawings, the MRI transfer table 10 includes a pair of side railings, each side railing being indicated generally by the numeral 150. Each side railing 150 includes a lower member 150A and an upper member 150B. The upper member 150B is rotatable with respect to the lower member 150A by conventional means. That is, the upper member 150B is rotatable from its operative position shown in FIG. 1 to a downward inoperative position. When the side railings 150 assumes the downward inoperative position, this enables a patient to be easily placed on the patient support 14 or removed therefrom.

Figure 1A:
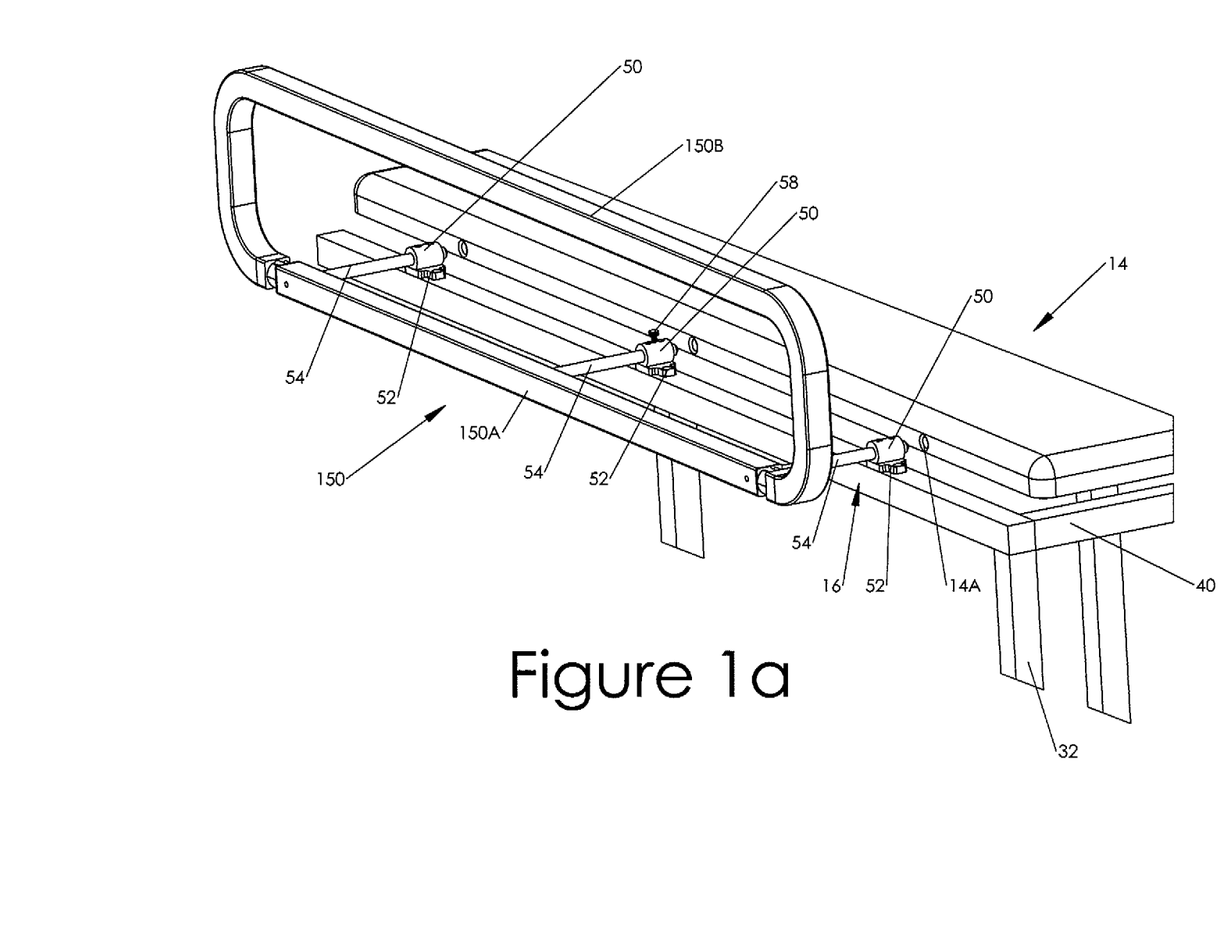
FIG. 1a is a fragmentary perspective view of the MRI transfer table showing the patient support disconnected from the mobile frame structure of the transfer table.

A part of the connecting structure is integrated into the side railings 150. In particular, there is provided a series of connecting pins 54 that project inwardly from each side railing 150. This is particularly illustrated in FIG. 1a. Connecting pins 54 are designed to be inserted into apertures or receivers 14A that are provided in the side edges of the patient support 14. See FIG. 1a.

Also forming a part of the connecting structure is a series of sleeves 50 that are mounted to upper supports 36 and 38 by mounts 52. Sleeves 50 are particularly spaced to align with the connecting pins 54 extending from the side railings 150. Each sleeve 50 includes both a horizontal bore and a vertical bore. The connecting pins 54 slide into the horizontal bores of the sleeves 50. Each connecting pin 54 has at least one transverse opening formed therein for receiving a locking pin. In addition to the horizontal bore, each sleeve 50 includes a vertical bore for receiving a locking pin 58. When the side railings assume their innermost position as shown in FIG. 1, the respective connecting pins 54 connect through the respective sleeves 50 into the apertures 14A formed in the side edges of the patient support 14. To lock the locking pins 54 in place, the locking pins 58 are inserted downwardly through the vertical bores of the sleeves 50 such that the locking pins extend through the transverse opening formed in the respective connecting pins 54. This securely anchors the connecting pins 54 in place and effectively connects the patient support 14 to the mobile frame structure 12.

It is appreciated that other forms of connectors could be utilized to secure the patient support 14 to the mobile frame structure. For example, the patient support 14 could be provided with receivers specifically designed to receive the locking pins 54 where the receivers could be disposed along the bottom edge surface of the patient support 14.

To detach the patient support 14 from the mobile frame structure 12, the locking pins 58 are removed from the sleeves 50. This enables the connecting pins 54 to be withdrawn from the apertures 14A in the patient support 14. When the connecting pins 54 are withdrawn from the patient support 14, then it follows that the patient support 14 and a patient laying thereon, can be removed from the mobile frame structure 12.

Note in FIG. 1 where the patient support 14 is essentially cantilevered off the mobile frame structure 12. That is, the upper frame members 36 and 38 that support the patient support 14 directly or indirectly when attached to the mobile main frame structure 12 are only supported at one end and intermediately between the ends. Thus, the left hand side of the patient support 14 as viewed in FIG. 1 is not directly supported by underlying structure. Further, as seen in FIG. 2, the left end portion of the MRI transfer table 10 is open except for the bottom frame member 24. Note the opening 42 shown in FIG. 2. This enables an MRI table 102 to be easily inserted underneath the patient support 14 and also enables the MRI table to engage the underside of the patient support 14 without any interference from the structural makeup of the MRI transfer table.

Figure 9:
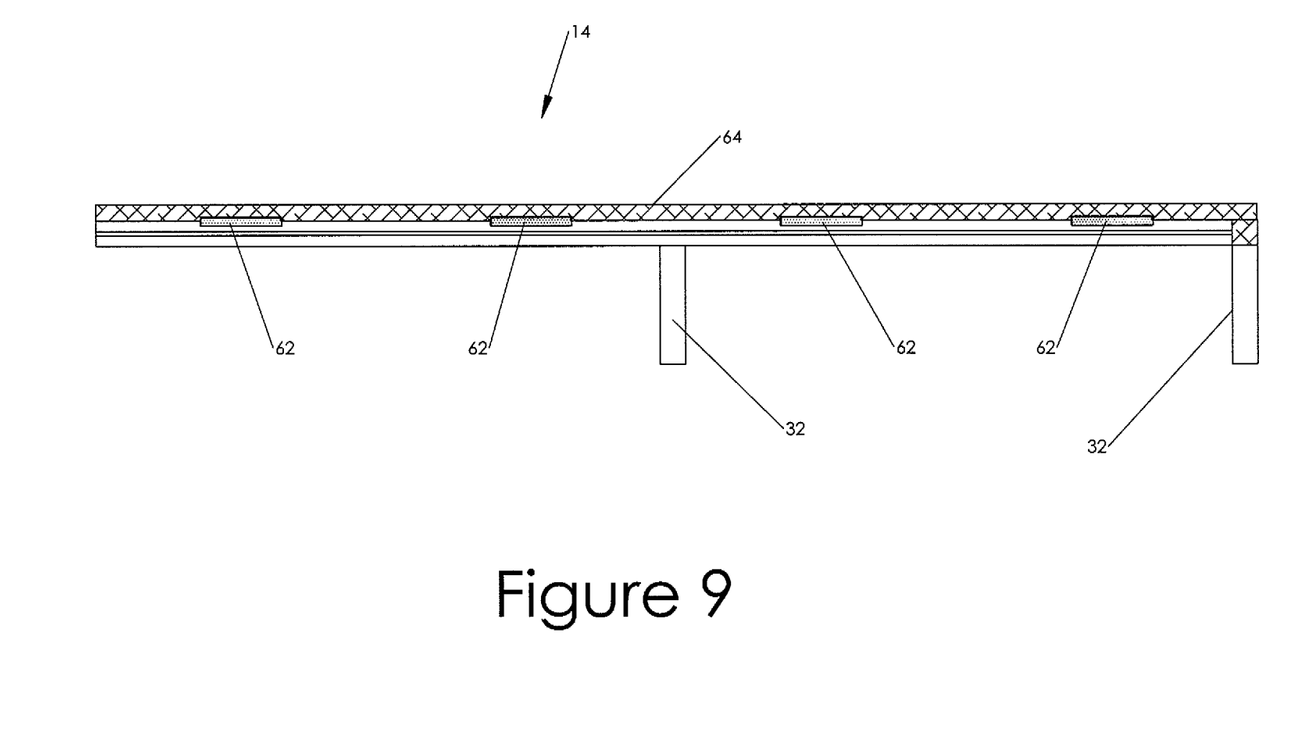
FIG. 9 is a fragmentary sectional view showing an alternate embodiment for the patient support.

FIG. 9 shows an alternate embodiment for the patient support 14. In this alternate embodiment, the patient support 14 includes a series of slats 62. Slats 62 seat into recesses formed in the upper members 36 and 38. Supported on the slats 62 is a non-metallic patient support surface 64.

Figure 10:
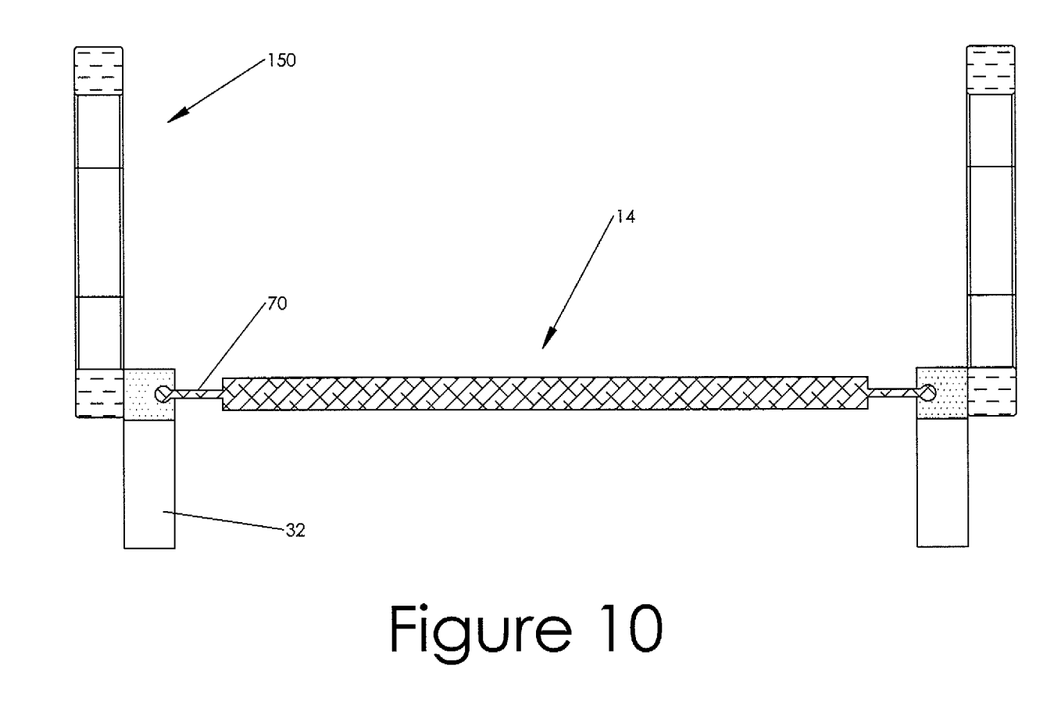
FIG. 10 is a fragmentary cross-sectional view showing another alternate design for the patient support.

FIG. 10 shows another alternative embodiment for the patient support 14. In the FIG. 10 embodiment, the patient support 14 is supported on the mobile frame structure 12 by a tongue-and-groove arrangement. More particularly, the upper frame members 36 and 38 along the inside edges include elongated grooves that extend substantially the length of the MRI transfer table 10. Patient support 14 includes a tongue 70 that projects into these grooves. More particularly, as viewed in FIG. 10, the tongue 70 on each side of the patient support 14 includes a flange that extends outwardly from the edge of the patient support and disposed on the terminal end of the flange is a circular portion that is configured to be received in the grooves of the upper members 36 and 38. Accordingly, it is appreciated that the patient support 14 can slide longitudinally within the mobile frame structure 12. To remove the patient support 14, the patient support is moved towards the left end of the MRI transfer table as viewed in FIG. 1 until the tongue 70 exits the two grooves in the upper frame members 36 and 38. There would be provided means to lock or secure the patient support 14 in the mobile frame structure 12.

Turning to FIGS. 3-8, there is shown therein an MRI apparatus indicated generally by the numeral 100. MRI apparatus 100 includes an extendable MRI table 102 that is moveable outwardly with respect to the inlet opening of the MRI apparatus.

Figure 3:
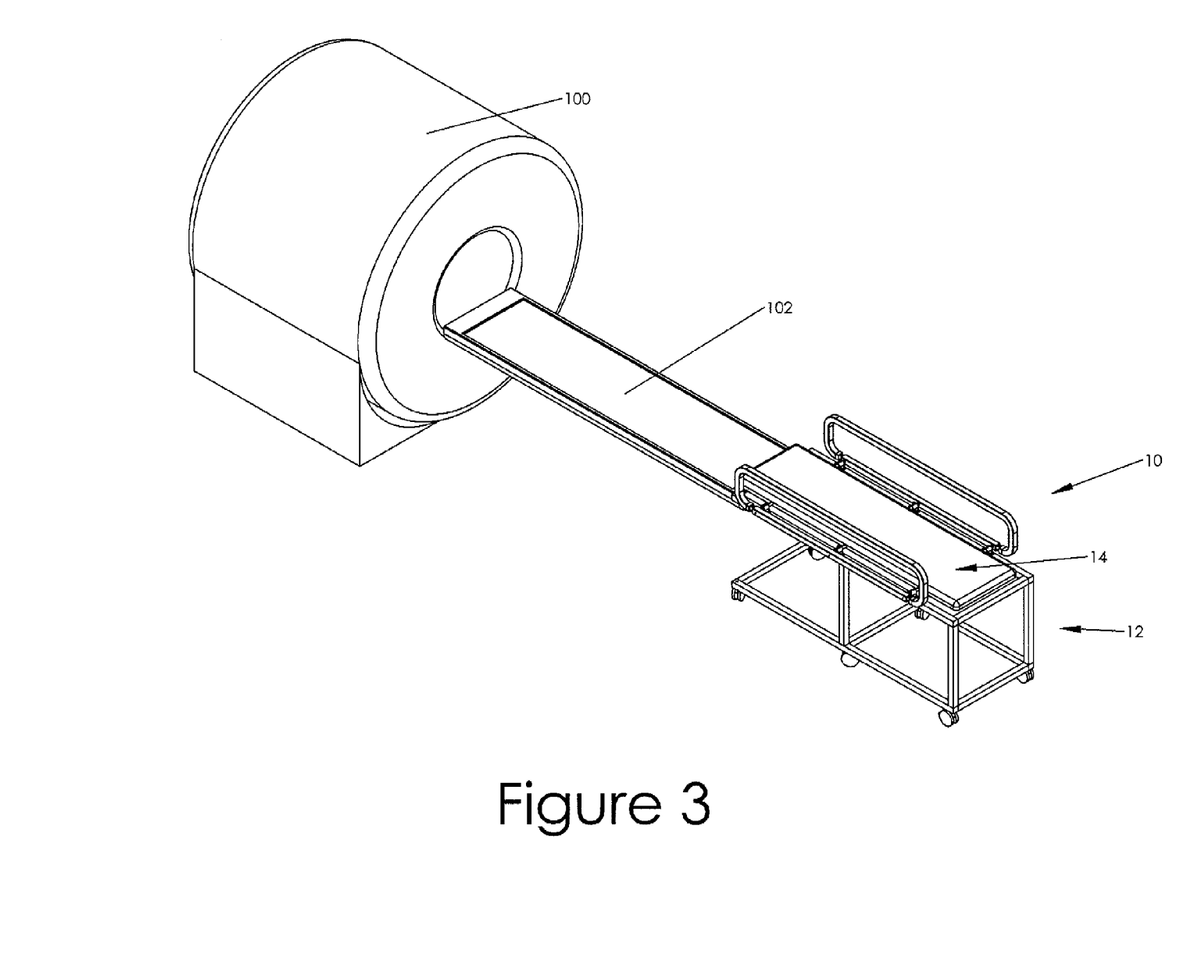
FIG. 3 is a perspective view showing the MRI transfer table being aligned with the MRI table.
Figure 4:
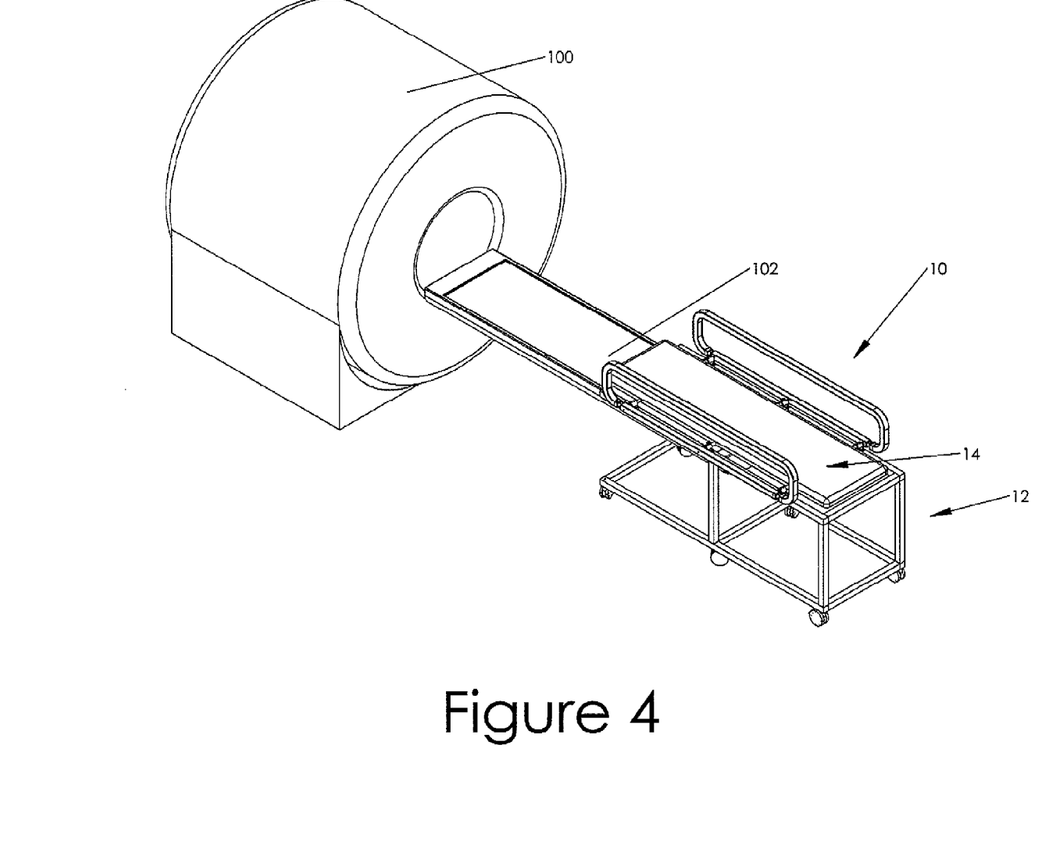
FIG. 4 is a perspective view showing the MRI transfer table being rolled over the MRI table.
Figure 5:
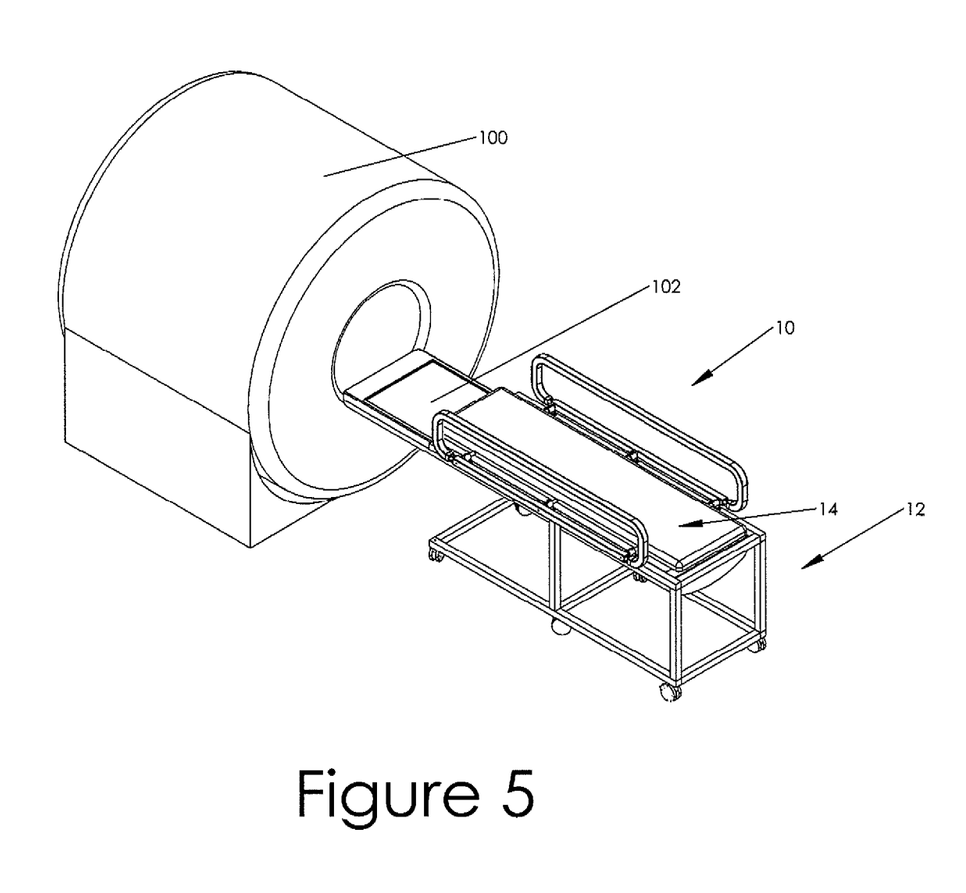
FIG. 5 is a perspective view showing the MRI transfer table being moved further towards the MRI apparatus and the MRI table being further projected underneath the patient support of the MRI transfer table.
Figure 6:
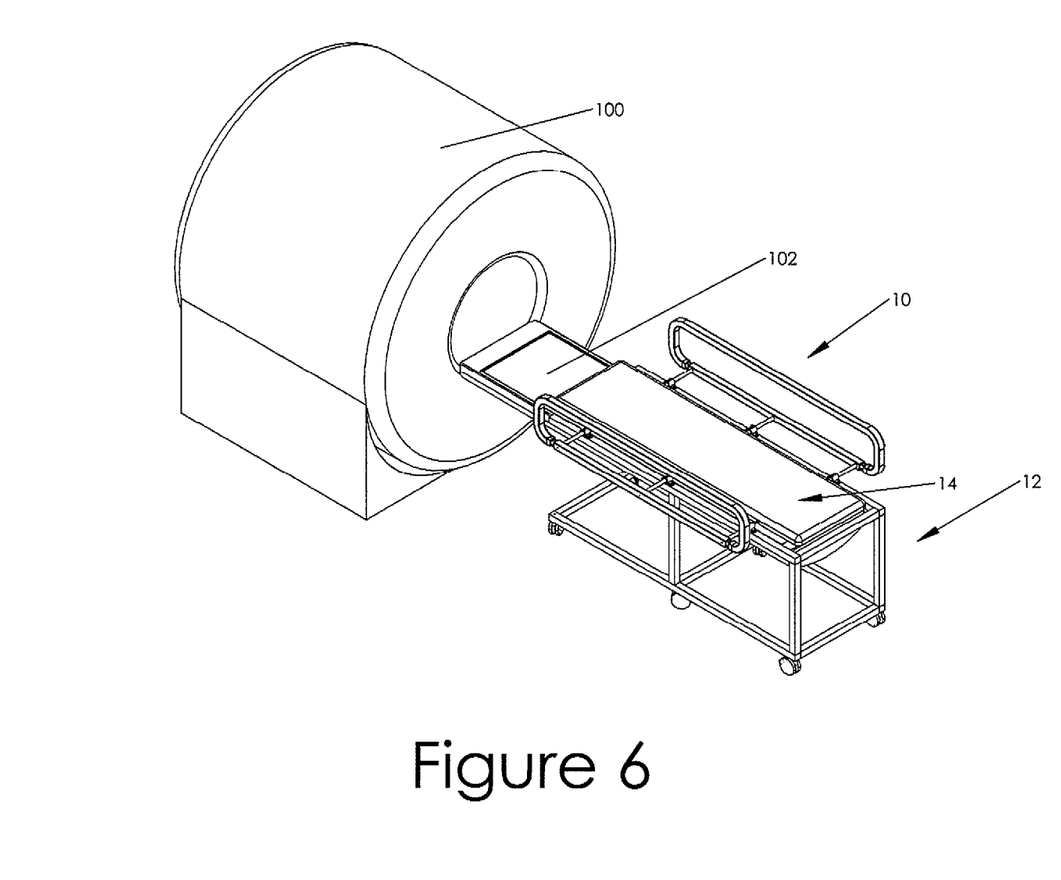
FIG. 6 is a perspective view showing how the patient support is disconnected from the mobile frame structure of the MRI transfer table.
Figure 7:
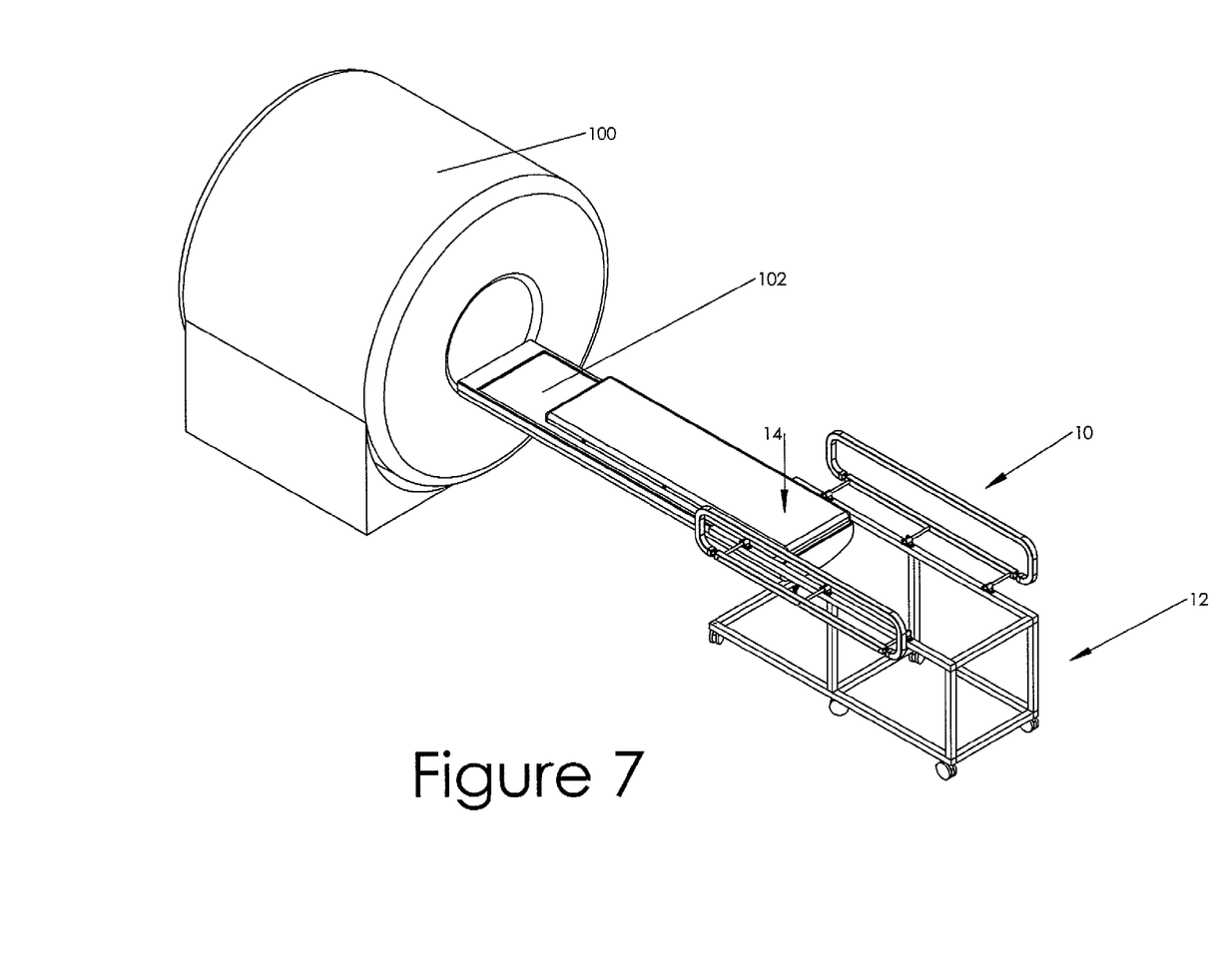
FIG. 7 is a perspective view showing the mobile support structure being removed from the MRI table.
Figure 8:
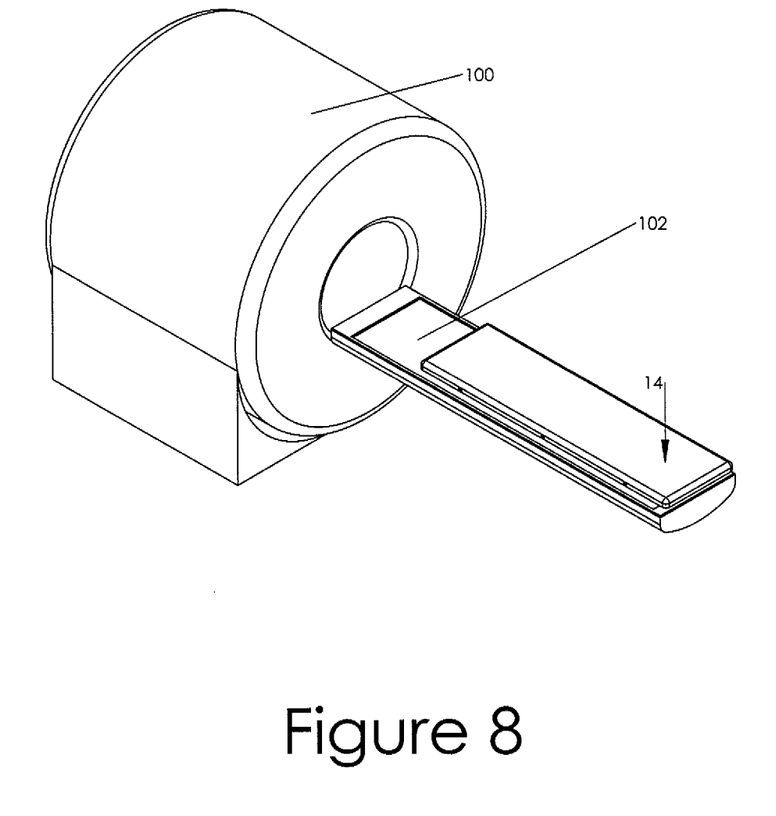
FIG. 8 is a perspective view showing the patient support of the MRI transfer table being disposed on the MRI table.

In use, the MRI transfer table 10 with a patient supported on the patient support 14 is moved to a position adjacent the inlet end of the MRI apparatus 100 (FIG. 3). It is noted that the open frame area 42 of the MRI transfer table show in FIG. 2 faces the inlet of the MRI apparatus. Once the MRI transfer table 10 is properly positioned, the MRI table 102 is projected underneath the patient support 14 (FIGS. 4-6). Note that the open end 42 of the MRI transfer table enables the MRI table 102 to be projected into the frame structure of the MRI transfer table 10 without any interference. The MRI table 102 is projected a sufficient distance underneath the patient support 14 such that a substantial area of the patient support 14 over-lies the MRI table 102 (FIG. 5). Next the MRI table is elevated to where the top surface thereof lies closely adjacent to the bottom surface of the patient support 14. Now the patient support 14 is separated from the mobile frame structure 12. This is accomplished with respect to the embodiment shown in FIG. 1 by simply retracting the connecting pins 54 from the openings 14A of the patient support. Once the connecting pins 54 are retracted, the patient support 14 is totally supported by the MRI table 102 (FIG. 6). Now the mobile frame 12 can be retracted or moved from the MRI apparatus, and removed from the examination area surrounding the MRI apparatus (FIG. 7).

When it is time to retrieve the patient, the process just described is reversed. That is, the mobile frame structure 12 without the patient support 12 can be positioned about an extended MRI table 102 such that the patient support 14 can be attached to the mobile frame structure 12. Now the patient, aboard the patient support 14, can be moved by the MRI transfer table 10 from the MRI examination area by simply moving the mobile frame structure 12.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. An MRI transfer table configured for transferring patients wherein the table can be adapted to be used with an MRI table, the transfer table comprising:
   a. a mobile frame structure having a pair of sides and opposed ends and wherein the sides are longer than the ends including: (1) a lower frame; (2) an upper frame including at least two side supports; and (3) an interconnecting frame extending between the lower frame and the upper frame;
   b. an elongated, non-metallic patient support configured to be supported by the side supports of the upper frame;
   c. the elongated non-metallic patient support having a pair of sides and opposed ends and wherein the sides are longer than the ends;
   d. a series of connectors for detachably connecting the patient support to the upper frame of the mobile frame structure;
   e. the series of connectors being disposed on each side of the mobile frame structure and on each side of the patient support;
   f. the series of connectors engaging the opposite sides of the patient support for detachably connecting the patient support to the upper frame of the mobile frame structure; and
   g. the connectors being movable between a connected and disconnected position, and wherein in the connected position the patient support is attached and supported by the mobile frame structure, and wherein in the disconnected position the patient support is removed from the mobile frame structure; and
   h. a pair of side railings disposed on opposite sides of the patient support, and wherein the connectors include a plurality of connecting pins secured to each side railing and projecting therefrom.

2. The MRI transfer table of claim 1 further including about one end of the mobile frame structure a substantial opening allowing a substantial portion of an MRI table to be projected beneath the patient support.

3. The MRI transfer table of claim 1 wherein the upper frame is cantilevered on the interconnecting frame such that a substantial portion of the upper frame is not directly supported by the interconnecting frame.

4. The MRI transfer table of claim 1 wherein the interconnecting frame is comprised of at least two end posts and at least two intermediate posts, and wherein the end posts are generally located on one end portion of the MRI transfer table, and wherein the intermediate posts are located approximately midway between ends of the MRI transfer table.

5. The MRI transfer table of claim 1 wherein a series of receivers are located on the patient support for receiving the connectors.

6. The MRI transfer table of claim 5 wherein the connectors are supported by the upper frame of the mobile frame structure.

7. The MRI transfer table of claim 6 wherein a series of holders are attached to the upper frame of the mobile frame structure for holding the connectors.

8. The MRI transfer table of claim 6 wherein the connectors are laterally adjustable and project into the receivers in a connected position, and wherein the connectors lie outside the receivers in a disconnected position enabling the patient support to be detached from the mobile frame structure.

9. The MRI transfer table of claim 5 further including a locking pin used for locking the connectors in a fixed position.

10. The MRI transfer table of claim 1 wherein the lower frame is comprised of a box frame having a pair of longitudinal members, a pair of end members, and a pair of intermediate posts and a pair of end posts, and wherein the intermediate posts and the end posts are connected to the box frame and extend upwardly therefrom for supporting the upper frame.

11. The MRI transfer table of claim 1 further including side railings on the mobile frame member for movement between an operative position and an inoperative position.

12. The MRI transfer table of claim 1 wherein the patient support is comprised of wood or plastic or a combination of wood and plastic.

13. The MRI transfer table of claim 1 wherein the upper frame is cantilevered off the lower frame so as to form a substantial open space between the cantilevered upper frame and the lower frame and wherein the open space is sufficiently open such that an MRI table can be projected into the mobile frame structure and underneath the patient support.

14. The MRI transfer table of claim 13 wherein the interconnecting frame includes two end posts disposed on a first end portion of the MRI transfer table and which extend between the lower frame and the upper frame; a pair of intermediate posts located approximately midway between the first end portion of the MRI transfer table and a second opposite end portion of the MRI transfer table, and wherein the intermediate posts extend between the lower frame and the upper frame; and wherein there are no posts located on the second end portion opposite the first end portion such that substantially the entire area between the lower frame and the upper frame is clear of any substantial obstruction between the second end portion and the intermediate posts.

15. The MRI transfer table of claim 1 further including a series of apertures secured to the upper frame for receiving and holding the connecting pins when the connecting pins are connected to the patient support.

16. The MRI transfer table of claim 1 wherein the patient support includes a series of transverse slats supported on the upper frame and a patient support surface supported on the slats.

17. The MRI transfer table of claim 1 wherein the patient support and the upper frame are detachably connected together through a tongue-and-groove arrangement that enables the patient support to slide horizontally with respect to the upper frame.

\* \* \* \* \*